United States Patent
Frobert

(10) Patent No.: US 9,395,272 B2
(45) Date of Patent: Jul. 19, 2016

(54) METHOD OF DETECTING NITROGEN COMPOUNDS CONTAINED IN EXHAUST GASES, NOTABLY OF INTERNAL-COMBUSTION ENGINES

(71) Applicant: IFP Energies nouvelles, Rueil-Malmaison Cedex (FR)

(72) Inventor: Arnaud Frobert, Irigny (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 13/940,289

(22) Filed: Jul. 12, 2013

(65) Prior Publication Data

US 2014/0024128 A1    Jan. 23, 2014

(30) Foreign Application Priority Data

Jul. 17, 2012    (FR) .................... 12/02.027

(51) Int. Cl.
| | | |
|---|---|---|
| *G01N 15/00* | (2006.01) | |
| *G01N 31/22* | (2006.01) | |
| *G01N 31/00* | (2006.01) | |
| *G01M 15/10* | (2006.01) | |
| *F01N 3/20* | (2006.01) | |
| *F01N 11/00* | (2006.01) | |

(52) U.S. Cl.
CPC ............ *G01M 15/102* (2013.01); *F01N 3/208* (2013.01); *F01N 11/007* (2013.01); *F01N 2560/026* (2013.01); *F01N 2570/14* (2013.01); *F01N 2900/0402* (2013.01); *F01N 2900/0412* (2013.01); *F01N 2900/0416* (2013.01); *F01N 2900/1402* (2013.01); *F01N 2900/1616* (2013.01); *G01N 15/00* (2013.01); *G01N 31/00* (2013.01); *G01N 31/22* (2013.01); *Y02T 10/24* (2013.01); *Y02T 10/47* (2013.01); *Y10T 436/17* (2015.01); *Y10T 436/172307* (2015.01)

(58) Field of Classification Search
CPC .. C01M 15/102; C01M 15/00; G01M 15/102; G01M 15/00; G01N 15/102; G01N 15/00; B01D 53/346; B01D 53/34; B01D 53/00; Y10T 436/12; Y10T 436/00; Y10T 436/17; Y10T 436/179228; Y10T 436/178459; Y10T 436/177692; Y10T 436/100833
USPC .................................................. 436/109, 106
See application file for complete search history.

(56) References Cited

U.S. PATENT DOCUMENTS 7,575,931 B2 *    8/2009    Steichen et al. .............. 436/118
2004/0098974 A1    5/2004    Nieuwstadt et al.

FOREIGN PATENT DOCUMENTS

| EP | 2 226 480 A1 * | 9/2010 | ................ F01N 3/20 |
| WO | WO 2009/135016 A2 | 11/2009 | |
| WO | WO 2011/093771 A1 | 8/2011 | |

OTHER PUBLICATIONS

STN Search Report for U.S. Appl. No. 13/940,289, obtained on Feb. 18, 2016, pp. 1-83.*

* cited by examiner

*Primary Examiner* — Christine T Mui
(74) *Attorney, Agent, or Firm* — Fitch, Even, Tabin & Flannery LLP

(57) ABSTRACT

A method of detecting nitrogen compound emissions in exhaust gases treated with selective catalytic reduction achieved by injecting a reducing agent into the gases and by passing these gases through a catalyst include sending the signal collected by a gas detector arranged in the exhaust gas downstream from the catalyst and representative of the amount of NOx ($NOx_{sonde}$) at the catalyst outlet to a computing unit, decomposing this signal into a value representative of the effective NOx amount ($NOx_{réel}$) at the outlet of catalyst established by the SCR catalyst model, into a detector perturbation coefficient (k) and into a value representative of the ammonia amount ($NH_{3réel}$) via an integrated model so as to obtain $NOx_{sonde} = NOx_{réel} + k.NH_{3réel}$, evaluating coefficient (k) from this decomposition, and determining the presence of nitrogen compounds downstream from the catalyst when coefficient (k) is greater than or equal to 1.

13 Claims, 1 Drawing Sheet

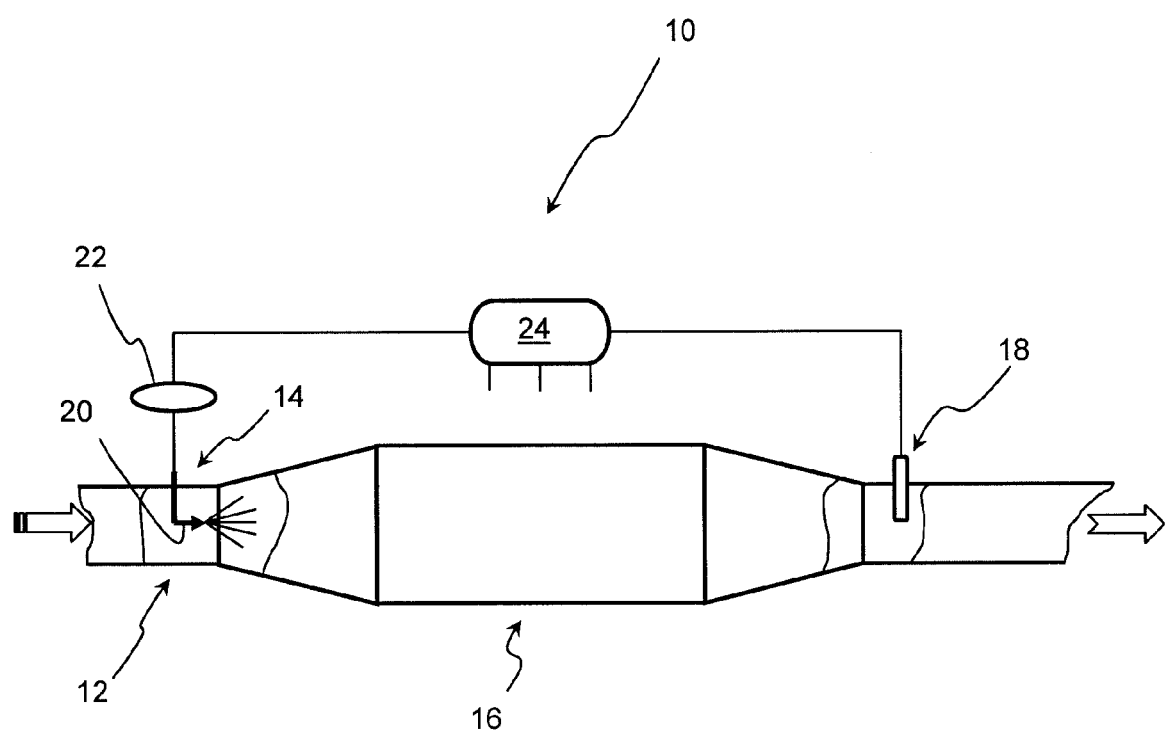

METHOD OF DETECTING NITROGEN COMPOUNDS CONTAINED IN EXHAUST GASES, NOTABLY OF INTERNAL-COMBUSTION ENGINES

FIELD OF THE INVENTION

The present invention relates to a method of detecting nitrogen compounds contained in exhaust gases.

It more particularly, but not exclusively, relates to exhaust gases circulating in the exhaust line of a combustion engine, in particular an internal-combustion engine.

BACKGROUND OF THE INVENTION

The phrase "exhaust gas" covers the result of the combustion of a fuel mixture in an internal-combustion engine, stationary or installed in a motor vehicle, as well as any other type of combustion result, such as fumes from a turbine or an oven that circulate in a chimney.

In general, the ignition of a fuel such as a motor fuel creates, under high temperature and high oxygen content conditions, gases such as nitrogen monoxide (NO), nitrogen dioxide ($NO_2$), more commonly referred to as NOx (nitrogen oxides).

These NOx are then discharged to the atmosphere and they present a danger, on the one hand, to people's health and, on the other hand, to the environment since they contribute to the formation of smog likely to attack the tropospheric ozone layer.

It is consequently necessary to provide means preventing discharge of these NOx into the atmosphere, for example by destroying them after they have formed.

To destroy these NOx, it is well known to conduct a chemical treatment operation such as a selective catalytic reduction, referred to as SCR (Selective Catalytic Reduction).

This operation consists in selectively reducing the NOx by means of a reducing agent on a dedicated catalyst. The reduction is referred to as selective because the reducing agent reduces the NOx and not the oxygen present in the mixture to be burned.

This reducing agent, in particular for use with an internal-combustion engine of a motor vehicle, is either ammonia (or a material that can decompose to ammonia), or a hydrocarbon, oxygenated or not, or a hydrocarbon mixture that can contain, partly or totally, one or more oxygenated hydrocarbons.

In the case of exhaust gas treatment with SCR using ammonia, the ammonia-based agent used is stored either in form of solid complexes, or in form of liquid precursors, such as urea in aqueous solution.

In the case of liquid precursors in form of urea, it is injected into the exhaust gas stream upstream from the catalyst. After this injection, the water contained in the urea is evaporated under the effect of the heat of the gas and the urea decomposes to ammonia and isocyanic acid.

For treatment with SCR using hydrocarbons, oxygenated or not, they are injected at the exhaust or they result from the combustion, in case of a late post-injection for example, and they react with the NOx contained in the exhaust gas. During this reaction, unstable complexes containing C, H, N and O form and they ideally decompose to carbon dioxide, water and dinitrogen.

Many other compounds however also form, such as hydrogen cyanide that can be present in an amount that is not insignificant, for example in the case of a treatment with SCR using ethanol.

As it is well known, devices allowing the injection of reducing agents to be managed are provided so as to ensure a sufficient injection for correctly reducing the NOx.

In this type of device, a gas detector notably sensitive to nitrogen oxides, more commonly known as NOx sonde, is arranged at the catalyst outlet and allows the amounts of gas discharged to be measured.

The output signal of this detector is sent to a computing unit intended for control and/or diagnosis of the reducing agent injection function and/or of the catalytic function. From this signal, the computing unit determines the amount of NOx contained in the exhaust gas at the catalyst outlet and this amount is then compared with a predetermined model. In case of a difference in relation to this model, the reducing agent injection setpoint is modified so as to reduce or even cancel this difference.

Although this device gives satisfactory results, it however involves considerable drawbacks.

Indeed, this device does not allow the presence of other compounds, such as isocyanic acid or hydrogen cyanide, to be detected.

The computing unit can thus not be informed of the presence of these compounds in the treated exhaust gas at the catalyst outlet and these compounds are discharged as they are to the atmosphere, where they can be harmful to living organisms.

The present invention aims to overcome the aforementioned drawbacks in a simple and inexpensive manner by using the devices already present on the exhaust line or the chimney.

SUMMARY OF THE INVENTION

The present invention thus relates to a method of detecting nitrogen compound emissions in exhaust gases treated with selective catalytic reduction achieved by injecting a reducing agent into the gases and by passing these gases through a catalyst, characterized in that the method consists in:
  sending to a computing unit the signal collected by a gas detector (18) arranged in the exhaust gas downstream from the catalyst and representative of the amount of NOx ($NOx_{sonde}$) at the catalyst outlet,
  decomposing this signal into a value representative of the effective NOx amount ($NOx_{réel}$) at the catalyst outlet established by the SCR catalyst model, into a detector perturbation coefficient (k) and into a value representative of the ammonia amount ($NH_{3réel}$) via an integrated model so as to obtain $NOx_{sonde}=NOx_{réel}+k.NH_{3réel}$,
  evaluating coefficient (k) from this decomposition,
  determining the presence of nitrogen compounds downstream from the catalyst when coefficient (k) is greater than or equal to 1.

The method can consist in introducing ammonia or a material that decomposes to ammonia as the reducing agent.

The method can consist in introducing urea as the reducing agent.

The method can consist in detecting the presence of isocyanic acid in the exhaust gas downstream from the catalyst when coefficient (k) is greater than or equal to 1 and when the reducing agent is ammonia or a material decomposing to ammonia.

The method can consist in introducing a hydrocarbon as the reducing agent.

The method can consist in introducing an oxygenated hydrocarbon as the reducing agent.

The method can consist in introducing ethanol as the reducing agent.

The method can consist in detecting the presence of isocyanic acid when coefficient (k) is greater than or equal to 1 and when the reducing agent is a hydrocarbon.

The method can consist in launching an alert sequence by the unit after detection of these nitrogen compounds.

BRIEF DESCRIPTION OF THE SOLE FIGURE

Other features and advantages of the invention will be clear from reading the description hereafter, given by way of non-limitative example, with reference to the accompanying sole FIGURE showing a NOx treatment device by SCR process that uses the present invention.

DETAILED DESCRIPTION

This sole FIGURE illustrates NOx treatment device by SCR process 10 arranged on an exhaust line 12. Exhaust gases coming from an internal-combustion engine (not shown) that can be static or installed in a motor vehicle circulate in this line.

This device comprises, in the direction of flow of the exhaust gases between an inlet E and an outlet S, reducing agent injection means 14, a SCR catalyst 16 and a gas detector in form of a NOx sonde 18 arranged downstream from this catalyst.

Of course, without departing from the scope of the invention, the reducing agent can also come from the combustion chamber of the engine in case of fuel post-injection for example.

In cases where the reducing agent does not come from the combustion chamber of the engine, these injection means comprise an injector 20 connected to an injection circuit 22 comprising all the elements (tank, pump, etc.) required for such an injection. This injector is arranged on the portion of the exhaust line upstream from the SCR catalyst in such a way that its nozzle opens into the exhaust line for spraying the reducing agent towards this catalyst.

Advantageously, the reducing agent is ammonia or a material generating ammonia by decomposition, such as urea, but any other agent such as a hydrocarbon, hydrogenated or not, can be used.

The device also comprises a computing and control unit 24 for controlling injection circuit 22, which is also connected to sonde 18. This computing unit contains tables with a SCR catalyst model allowing to know the amount of reducing agent to be injected in order to obtain the suitable NOx treatment in the catalyst, as well as an integrated phenomenological model for the ammonia amount at the catalyst outlet.

Thus, by means of the NOx sonde, this unit 24 knows at any time the amount of NOx leaving the catalyst and it thus allows to adjust the amount of reducing agent to be delivered in the exhaust line in order to obtain the desired efficiency.

Of course, this unit is also connected to various other detectors (not shown), such as exhaust gas temperature detectors, and it receives information on the operation of the internal-combustion engine so as to allow injection circuit 22 to be controlled.

During a test campaign on the device of the FIGURE, the applicant discovered that the NOx sonde is sensitive to nitrogen compounds and notably to isocyanic acid (HNCO) and hydrogen cyanide (HCN).

The applicant therefore developed a method allowing to identify these nitrogen compounds and to launch information or alert procedures for the user.

As it is well known for a conventional ammonia SCR treatment control system, the NOx emission difference is identified by means of the NOx sonde by comparing the signal sent by this sonde with information on the amount of NOx expected downstream from the SCR catalyst. This amount can notably be estimated by a phenomenological model stored in unit 24.

As it is widely acknowledged, a NOx sonde is designed for measuring NOx values.

It can however be perturbed by a sum of compounds $P_i$ that all perturb the sonde according to a coefficient $k_i$ with:

$$NOx_{sonde} = NOx_{réel} + \sum_i k_i \cdot P_i$$

Among the compounds that can perturb the sonde, the best known one is ammonia ($NH_3$). The other compounds whose perturbing power was observed by the applicant are HNCO (isocyanic acid) and HCN (hydrogen cyanide).

It is known from the literature that the perturbation related to ammonia corresponds to a perturbation coefficient k that is less than 1.

Now, under real conditions, in a vehicle for example, we can know:

$NOx_{sonde}$: the amount of NOx measured or estimated by means of sonde 22, $NOx_{réel}$: the effective NOx amount at the outlet of catalyst 16 established by the SCR catalyst model via an integrated model in the engine control unit or a non-perturbed sonde or a laboratory type "cabinet" measurement, $NH_{3réel}$: the ammonia amount via an integrated model in the engine control unit or a non-perturbed sonde or a laboratory type "cabinet" measurement.

From that, it is thus possible to calculate coefficient k as follows:

$$NOx_{sonde} = NOx_{réel} + k \cdot NH_{3réel}$$

$$\text{therefore } k = \frac{NOx_{sonde} = NOx_{réel}}{NH_{3réel}}$$

If k<1, it can be considered that there is a perturbation due to ammonia.

If k>1, ammonia alone cannot explain the perturbation of the sonde and it is admitted that a perturbing nitrogen compound is present in the exhaust gas.

Thus, in case of SCR treatment with ammonia (or a material that can decompose to ammonia), a not insignificant amount of isocyanic acid (HNCO) is present at the catalyst outlet, in case of SCR treatment with a hydrocarbon and in particular ethanol, a not insignificant amount of hydrogen cyanide (HCN) is present.

In both cases, these polluting emissions can indicate a significant malfunction during NOx treatment by the catalyst or upon the reducing agent delivery.

The computing unit therefore launches one or more alert sequences in order to inform the user of the presence of unwanted nitrogen compounds in the exhaust gas, which indicates a malfunction of the depollution function.

For example, the unit sends a signal to the on-board computer (OBD—On-Board Diagnostic) to report this anomaly, which can generate the actuation of an alert indicator light or a request for intervention by a specialist.

It can therefore be noted that taking account of the sonde perturbation by isocyanic acid (HNCO) and by hydrogen cyanide (HCN) is thus useful for the diagnosis of the NOx treatment function using SCR.

Of course, the above description of the method can also be applied to other types of exhaust gases than those from a combustion engine.

It can notably be applied in connection with the fumes coming from another combustion, from a turbine or an oven for example, and circulating in a discharge chimney comprising a NOx treatment device by SCR 10.

The invention claimed is:

1. A method of detecting nitrogen compound emissions in exhaust gases treated with selective catalytic reduction achieved by injecting a reducing agent into the gases and by passing these gases through a catalyst, characterized in that the method consists in:
    sending to a computing unit the signal collected by a gas detector arranged in the exhaust gas downstream from the catalyst and representative of the amount of NOx ($NOx_{sonde}$) at the catalyst outlet,
    decomposing this signal into a value representative of the effective NOx amount ($NOx_{réel}$) at the outlet of the catalyst established by the SCR catalyst model, into a detector perturbation coefficient (k) and into a value representative of the ammonia amount ($NH_{3réel}$) via an integrated model so as to obtain $NOx_{sonde} = NOx_{réel} + k.NH_{3réel}$,
    evaluating coefficient (k) from this decomposition,
    determining the presence of nitrogen compounds downstream from the catalyst when coefficient (k) is greater than or equal to 1.

2. A method as claimed in claim 1, characterized in that it consists in introducing ammonia or a material that decomposes to ammonia as the reducing agent.

3. A method as claimed in claim 1, characterized in that it consists in introducing urea as the reducing agent.

4. A method as claimed in claim 1, characterized in that it consists in detecting the presence of isocyanic acid in the exhaust gas downstream from catalyst when coefficient (k) is greater than or equal to 1 and when the reducing agent is ammonia or a material decomposing to ammonia.

5. A method as claimed in claim 1, characterized in that it consists in introducing a hydrocarbon as the reducing agent.

6. A method as claimed in claim 5, characterized in that it consists in introducing an oxygenated hydrocarbon as the reducing agent.

7. A method as claimed in claim 5, characterized in that it consists in introducing ethanol as the reducing agent.

8. A method as claimed in claim 1, characterized in that it consists in detecting the presence of isocyanic acid when coefficient (k) is greater than or equal to 1 and when the reducing agent is a hydrocarbon.

9. A method as claimed in claim 1, characterized in that it consists in launching an alert sequence by the computing unit after detection of these nitrogen compounds.

10. Use of the method as claimed in claim 1 for exhaust gases circulating in the exhaust line of an engine, notably an internal-combustion engine.

11. A method as claimed in claim 1, wherein the exhaust gases comprise fumes resulting from a combustion in a turbine or an oven.

12. A method as claimed in claim 1, wherein the gas detector comprises a $NOx_{sonde}$ sensitive to nitrogen oxides and a nitrogen compound in addition to nitrogen oxides.

13. A method as claimed in claim 12, wherein the $NOx_{sonde}$ is sensitive to one of isocyanic acid and hydrogen cyanide.

* * * * *